US006225622B1

(12) United States Patent
Navarro

(10) Patent No.: US 6,225,622 B1
(45) Date of Patent: May 1, 2001

(54) DYNAMIC RADIATION SCANNING DEVICE

(76) Inventor: Daniel Navarro, 601 NE. Emerson St., Port St. Lucie, FL (US) 34093

( * ) Notice: Subject to any disclaimer, the term of this patent is extended or adjusted under 35 U.S.C. 154(b) by 0 days.

(21) Appl. No.: 09/127,433

(22) Filed: Jul. 31, 1998

(51) Int. Cl.[7] ..................................................... G01T 1/20
(52) U.S. Cl. ...................... 250/252.1; 250/374; 378/207
(58) Field of Search ............................ 250/252.1, 363.09, 250/370.07, 374, 375, 491.1; 378/207

(56) References Cited

U.S. PATENT DOCUMENTS

| | | | |
|---|---|---|---|
| 4,538,071 | * 8/1985 | Bardoux et al. | ................... 250/505.1 |
| 4,988,866 | 1/1991 | Westerlund . | |
| 5,006,714 | 4/1991 | Attix . | |
| 5,511,107 | * 4/1996 | Sliski | ................................... 378/207 |
| 5,621,214 | 4/1997 | Sofield . | |
| 5,905,263 | * 5/1999 | Nishizawa et al. | ................... 250/268 |

* cited by examiner

*Primary Examiner*—Constantine Hannaher
*Assistant Examiner*—Albert Gagliaroi
(74) *Attorney, Agent, or Firm*—McHale & Slavin

(57) ABSTRACT

The present invention is a dynamic radiation scanning system for detecting radiation dosimetry of a beam emitted along an axis from a radiotherapy treatment machine and a method for its use. The system contains a dosimetry probe to sense photons and electrons, a dynamic phantom body formed from a material having a density approximating that of the human body, a gantry mounting assembly rigidly attached to the radiotherapy machine for positioning of the phantom body, and a lead screw assembly rigidly affixed to the gantry for providing coplanar movement of the dynamic phantom within a plane perpendicular to the axis of radiation emission. Movement of the dynamic phantom through a series of locations is carried out at varying depths and angles so as to provide sufficient data to determine variations in beam uniformity, thereby providing for simple and reliable testing and calibration of the machine.

18 Claims, 2 Drawing Sheets

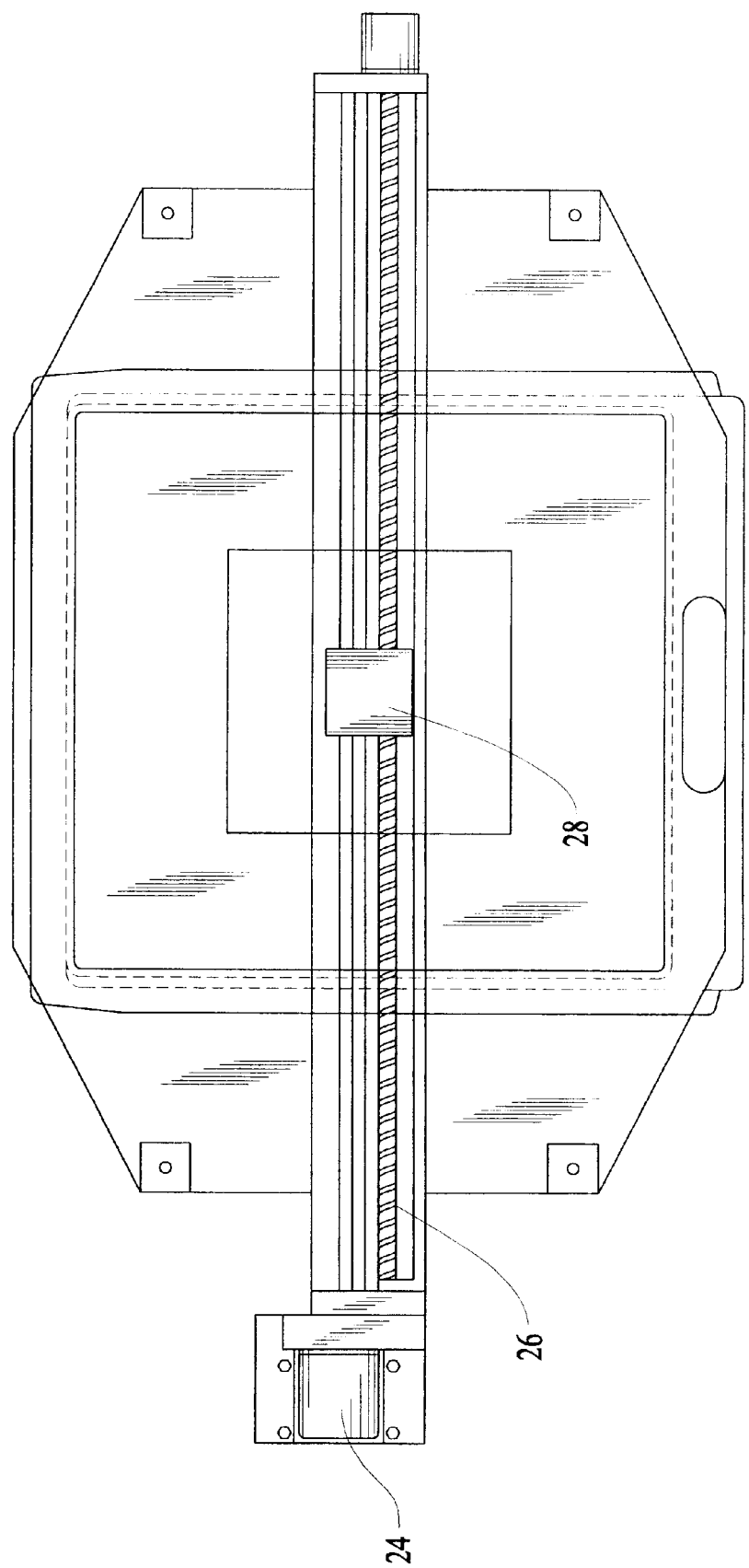

DYNAMIC RADIATION SCANNING DEVICE

FIELD OF THE INVENTION

This invention relates to a method and device for scanning of the radiation field emitted by a linear accelerator or other radiation producing device and particularly relates to the use of a movable small phantom carrying a radiation detector, usually an ion chamber, which moves together with the phantom.

BACKGROUND OF THE INVENTION

Various well-known medical techniques for the treatment of malignancies involve the use of radiation. Radiation sources, for example medical linear accelerators, are typically used to generate radiation to a specific target area of a patient's body. Use of appropriate dosimetry insures the application of proper doses of radiation to the malignant areas and is of utmost importance. When applied, the radiation produces an ionizing effect on the malignant tissue, thereby destroying the malignant cells. So long as the dosimetry of applied radiation is properly monitored, the malignancy may be treated without detriment to the surrounding healthy tissue. Accelerators may be utilized, each of which have varying characteristics and output levels. The most common type of accelerator produces pulse radiation, wherein the output has the shape of a rectangular beam with a cross-sectional area which is typically between 16 and 1600 square centimeters. Rectangular or square shapes are often changed to any desired shape using lead or cerrobend blocks, using molds and casting procedures. More advanced accelerators use multileaf collimators. Other accelerators are continuous or nonpulsed such as cobalt radiation machines; and accelerators that utilize a swept electron beam, which sweep a very narrow electron beam across the treatment field by means of varying electromagnetic fields.

To ensure proper dosimetry, linear accelerators used for the treatment of malignancies must be calibrated. Both the electron and photon radiation must be appropriately measured and correlated to the particular device. The skilled practitioner must insure that both the intensity and duration of the radiation treatment is carefully calculated and administered so as to produce the therapeutic result desired while maintaining the safety of the patient. Parameters such as flatness, symmetry, radiation and light field alignment are typically determined. The use of too much radiation may, in fact, cause side effects and allow destructive effects to occur to the surrounding tissue. Use of an insufficient amount of radiation will not deliver a dose that is effective to eradicate the malignancy. Thus, it is important to be able to determine the exact amount of radiation that will be produced by a particular machine and the manner in which that radiation will be distributed within the patient's body. In order to produce an accurate assessment of the radiation received by the patient, some type of pattern or map of the radiation at varying positions within the patient's body must be produced. These profiles correlate 1) the variation of dose with depth in water generating percent depth dose profiles and 2) the variation of dose across a plane perpendicular to the radiation source generating the cross beam profiles. These particular measurements of cross beam profiles are of particular concern in the present invention. Although useful for other analyses, the variation in the beam uniformity of the radiation field regardless of gantry orientation is the main purpose of this device.

One existing system for measuring the radiation that is produced by medical linear accelerators utilizes a large tank on the order of 50×50×50 cm filled with water. A group of computer controlled motors move the radiation detector through a series of pre-programmed steps beneath the water's surface. Since the density of the human body closely approximates that of water, the water-filled tank provides an appropriate medium for creating a simulation of both the distribution and the intensity of radiation which would likely occur within the patient's body. The aforementioned tank is commonly referred to as a water phantom. The radiation produced by the linear accelerator will be directed into the water in the phantom tank at which point the intensity of the radiation at varying depths and positions within the water can be measured with the radiation detector. As the radiation penetrates the water the direct or primary beam is scattered by the water, in much the same way as when the radiation beam impinges upon the human patient. Both the scattered radiation as well as the primary radiation are detected by the ion-chamber, which is part of the radiation detector. The ion-chamber is essentially an open air capacitor which produces an electrical current that corresponds to the number of ions produced within its volume. The detector is lowered to a measurement point within the phantom tank and measurements are taken over a particular time period. The detector can then be moved to another measurement point where measurements are taken as the detector is held in the second position. At each measuring point a statistically significant number of samples are taken while the detector is held stationary.

Several prior art devices are known to teach systems for ascertaining the suitable dosimetry of a particular accelerator along with methods for their use.

U.S. Pat. No. 5,621,214, issued Apr. 15, 1997, to Sofield, is directed to a radiation beam scanner system which employs a peak detection methodology. Except for the peak detection, this system operates like any other conventional scanning system, using two ion chamber detectors, a signal and a reference detector. In use, the reference detector remains stationary at some point within the beam while the signal detector is moved continuously by the use of electrical stepper motors.

U.S. Pat. No. 4,988,866, issued Jan. 29, 1991, to Westerlund, is directed toward a measuring device for checking of radiation fields from treatment machines for radiotherapy. This device comprises a measuring block that contains radiation detectors arranged beneath a cover plate and provided with field marking lines and an energy filter. The detectors are connected to a read out unit for signal processing and presentation of measurement values. Westerlund arranges the dose monitoring calibration detectors in a particular geometric pattern to determine homogeneity of the radiation field. In use, the measuring device is able to simultaneously check the totality of radiation emitted by a single source of radiation at varying positions within the measuring block. Although Westerlund's does not use a water phantom, his device is nevertheless limited in that all of the ionization detectors are in one plane. This does not yield an appropriate threedimensional assessment of the combination of scattering and direct radiation which would normally impinge the human body undergoing radiation treatment. Thus, accurate dosimetry in a real-life scenario could not be readily ascertained by the use of the Westerlund device.

U.S. Pat. No. 5,006,714, issued Apr. 9, 1991, to Attix utilizes a particular type of scintillator dosimetry probe which is manufactured from a material that approximates water or muscle tissue in atomic number and electron density. Attix indicates that the use of such a detector minimizes perturbations in a phantom water tank. While recognizing the use of a polymer material which is similar to water or muscle tissue in atomic number and electron density, Attix nevertheless requires the use of a cumbersome phantom water tank.

Additionally, there is an apparatus called a Wellhofer "bottle-ship" which utilizes a smaller volume of water than the conventional water phantom. The Wellhofer device still utilizes a timing belt and motor combination to move the detector through the water, thus requiring a long initial set-up time. Lastly, the Wellhofer device still operates on the principle of moving the detector through the phantom body, while the instant device moves a substantially smaller (15× 15×15 cm) plastic phantom body through the radiation field.

Thus, there exists a need for a device that is capable of quickly and accurately detecting both scattering and direct radiation components from radiation devices without requiring the use of a large and cumbersome water phantom.

SUMMARY OF THE INVENTION

The present invention is based upon the general principle of scanning radiation by the use of a radiation detector attached to a moving phantom. This principle states that the dynamic component of the scanning system becomes the phantom instead of the radiation detector used in conventional scanning methods. The theory behind conventional scanning is that the use of a large water phantom results in the scattering of the directly applied radiation in the large water tank in a manner similar to that which occurs when this direct radiation impinges upon the human body being treated. It has now been observed that the majority of the scatter contribution of this radiation component, in actuality, comes from a comparatively small volume very near to the ion-chamber itself. Therefore, moving this small volume together with the radiation detector provides radiation scanning measurements equivalent to those achieved when a large water phantom is employed.

A specially designed gantry mounting assembly for the linear accelerator holds a scanning guide which is attached to a phantom body made of a polymer material such as an acrylic, or the like material of similar and appropriate density. It has been determined that the acrylic material has a density similar to that of water and that the scatter which occurs in the enclosed material is substantially equivalent to that which occurs within the human body. It should be noted that the measurements taken are not absolute values, but relative measurements expressed in percent relative to a selected value. An appropriately sized block of acrylic or similar material, having a plurality of recesses adapted to receive the radiation detector, is affixed to the gantry mount assembly and at least one radiation detector is inserted therein. The recesses which are not being utilized are filled with a plug of the acrylic or similar material during the scanning procedure. The "dynamic phantom", including the ion chamber therein, is then moved through the radiation field. Movement is accomplished via the use of a lead screw assembly, which is essentially a worm gear rotated via a stepper motor and to which the dynamic phantom is operatively attached. Rotation of the worm gear results in coplanar movement of the dynamic phantom, in a plane which is perpendicular to the axis of emission of the radiant beam, and irrespective of the angle of the radiotherapy machine relative to the patient's body. This construction allows for rapid setup and calibration of the system, often in as little as about seven minutes as opposed to the twenty to thirty minutes needed to calibrate a water phantom apparatus.

Scanning and analyzing of the various radiation parameters of interest is carried out at varying angles and depths, wherein the only movement which occurs is the movement of the dynamic phantom itself, in and around the linear accelerator. The device is capable of utilizing isocentric scanning, for example scans are performed at a Source Axis Distance of 100 cm (SAD); or non-isocentric scanning techniques may be employed, e.g. 100 cm SSD (Source Surface Distance). The device is able to scan at virtually any arbitrary depth for field sizes up to 40×40 centimeters, at any radiotherapy machine angle, and in either the radial or transverse direction in simplified models.

As in conventional radiation scanning techniques, the process is conducted by remote control utilizing computer programs which control the motion of the system and produce analyses of the data produced thereby. The dynamic phantom of the present invention is capable of measuring both photons and electrons and is further adaptable to any linear accelerator.

Thus, it is an objective of the present invention to provide a convenient technique for measuring the most commonly verified parameters of radiation beams.

It is a further objective of the present invention to describe a procedure for utilizing a small dynamic phantom which allows direct measurement of cross plots for photons and cross plots and percentage depth dose for electrons.

It is yet another objective of the present invention to provide a method and apparatus for radiation detection and measurement which utilizes rapid and accurate setup, and significantly reduces the measurement time required by traditionally used scanning systems.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWING

FIG. 2 is a cross-sectional view of the device as viewed upwardly from the bottom.

DETAILED DESCRIPTION OF THE PREFERRED EMBODIMENT

Figure 1:
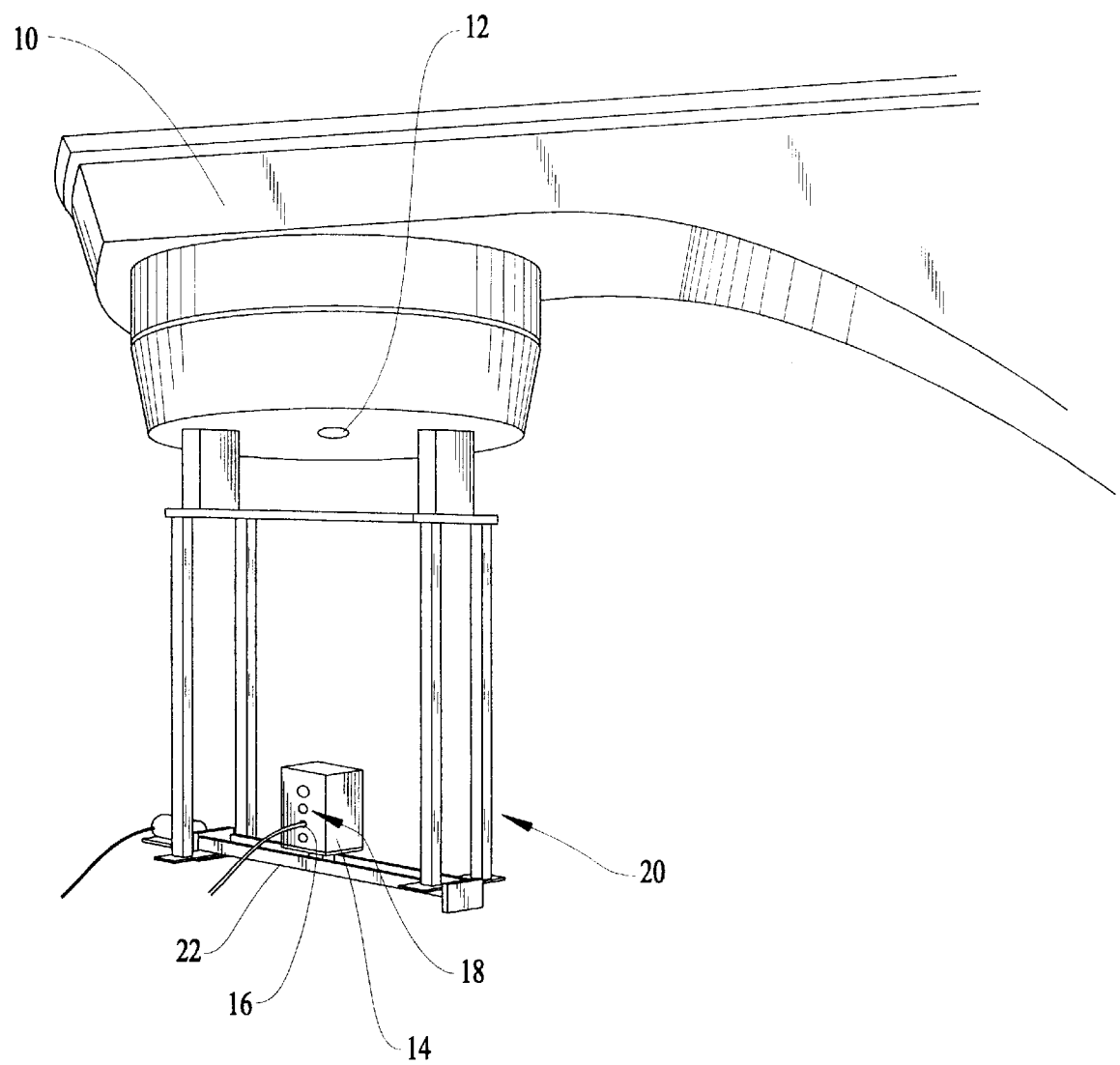
FIG. 1, is a pictorial view of a linear accelerator having the dynamic phantom of the present invention attached to the head of the gantry.

Now referring to FIGS. 1 and 2, a linear accelerator 10, emits a beam of radiation from the collimator area 12. The radiation beam is directed toward the dynamic phantom 14, which in a particular embodiment is a 15×15×15 cm acrylic block. The dynamic phantom contains a dosimetry probe 16, usually an ion chamber, which may be inserted in one of several recesses 18, which are positioned so as to enable the user to alter the depth of the dosimetry probe within the block. Exemplary depths are 1.5 cm (depth of maximum radiation intensity for 6MV), 3 cm (depth of maximum radiation intensity for 18MV), 5 cm and 10 cm. Those recesses which are not being utilized during the scanning procedure are plugged with an insert of material equal to that which forms the block. The gantry 20 is mounted on the accelerator and rigidly supports the dynamic phantom on a horizontal rail 22 which has a computer controlled stepper motor 24 attached to one end thereof. In operation, the linear accelerator is activated and the beam of radiation is emitted therefrom and impinges the dynamic phantom acrylic block. Direct radiation permeates the block and impinges upon the probe. Simultaneously, scattering radiation is also produced by virtue of the radiation beam impinging the acrylic block, which simulates the scattering radiation which occurs in a human patient being treated by such a radiation beam, and is also detected by the probe. The computer which controls the stepper motor is operatively attached to a lead screw assembly which comprises a worm gear 26 which is operatively associated with the dynamic phantom support bracket 28. As the stepper motor receives instructions to rotate the worm gear, this rotary movement is translated into horizontal displacement of the dynamic phantom through a series of locations designed to gather data regarding the variation of the radiation intensity through the field. While the field is characterized as "horizontal" as depicted in the figures, the displacement is in any plane that is perpendicular to the axis of emission of radiation from the radiotherapy machine, said plane being at a distance defined by positioning of the probe within the dynamic phantom block. The block is sized in such a way that the total of direct and scattering radiation represents virtually 100 percent of the radiation to which a patient will be exposed. In a particularly preferred embodiment, the block is 15×15×15 cm. Any additional radiation which occurs due to scattering outside the area of the dynamic phantom block has been determined to be of no clinical significance. After having been traversed through a first series of movements directed by the stepper motor, the depth of the probe within the block may be changed by moving it to an alternative recess. The block may then be stepped through a similar series of movements and further data is gathered. After moving the dynamic phantom through several such series at varying depths and radiotherapy machine angles, the computer will have gathered sufficient data to form a graphical analysis of the actual radiation to which a patient would be exposed during radiation therapy. The elimination of the large water tank utilized in the prior art allows the present device to be set up very quickly without the need for movement of a large tank, filling the tank with water and subsequently having to empty the water from the tank. The use of the lead screw assembly provides an accuracy of positioning of 0.1 mm and an accuracy of percentage dose measurement better than 0.5%. In addition, this device does not suffer from the mechanical failures which have often occurred in the past, when the stepper motors are utilized underwater. Failures due to corrosion, short circuiting and build up of dirt and sediment due to the underwater environment in which the probe was utilized are eliminated by the instant invention.

The present invention thus provides a reliable means of accurately and quickly determining the efficacy of a radiation producing device. By utilizing the dynamic phantom of the present invention a radiation physicist may accurately and repeatedly determine the beam radiation uniformity at any gantry angle. Thus the viability and accuracy of the machine may be easily determined by the clinical physicist as well as by the manufacturers of the accelerators.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

What is claimed is:

1. A dynamic radiation scanning system for detecting radiation dosimetry of a beam emitted along an axis from a radiotherapy treatment machine comprising:

at least one dosimetry probe constructed and arranged to sense photons and electrons;

a dynamic phantom body formed from a material having a density approximating that of the human body and having a plurality of recesses for receipt of one or more of said probes therein;

a gantry mounting assembly rigidly attached to said radiotherapy machine for positioning of said phantom body; and a lead screw assembly rigidly affixed to said gantry for providing coplanar movement of the dynamic phantom within a plane perpendicular to the axis of radiation emission;

whereby movement of the dynamic phantom through a series of locations is carried out at varying depths so as to provide sufficient data to determine variations in beam uniformity.

2. The dynamic radiation scanning system according to claim 1, wherein the dosimetry probe is an ion chamber.

3. The dynamic radiation scanning system according to claim 1, wherein the material utilized for the dynamic phantom is an acrylic.

4. The dynamic radiation scanning system according to claim 1, wherein the coplanar movement is isocentric.

5. The dynamic radiation scanning system according to claim 1, wherein the coplanar movement is nonisocentric.

6. The dynamic radiation scanning system according to claim 1, wherein the scanning depth is between 1.5 cm and 10 cm.

7. The dynamic radiation scanning system according to claim 1, wherein the radiotherapy treatment machine is a linear accelerator.

8. The dynamic radiation scanning system according to claim 1, wherein the radiotherapy treatment machine is a cobalt radiation machine.

9. The dynamic radiation scanning system according to claim 1, wherein the radiotherapy treatment machine is a swept electron beam accelerator producing photons or electrons.

10. A process for dynamically scanning to detect radiation dosimetry of a beam emitted along an axis from a radiotherapy treatment machine comprising:

providing at least one dosimetry probe constructed and arranged for sensing photons and electrons;

incorporating said at least one dosimetry probe within a dynamic phantom body formed from a material having a density approximating that of the human body and having a plurality of recesses for receipt of one or more of said probes therein;

providing a gantry mounting assembly rigidly attached to said radiotherapy machine for positioning of said phantom body;

providing a lead screw assembly rigidly affixed to said gantry for providing coplanar movement of the dynamic phantom within a plane perpendicular to the axis of radiation emission;

moving the dosimetry probe containing dynamic phantom to a series of locations at varying depths so as to provide sufficient data to determine variations in beam uniformity;

whereby testing and calibration of said radiotherapy machine is accomplished.

11. The process for dynamically scanning according to claim 10, wherein the dosimetry probe is an ion chamber.

12. The process for dynamically scanning according to claim 10, wherein the material utilized for the dynamic phantom is an acrylic.

13. The process for dynamically scanning according to claim 10, wherein the coplanar movement is isocentric.

14. The process for dynamically scanning according to claim 10, wherein the coplanar movement is nonisocentric.

15. The dynamic radiation scanning system according to claim 10, wherein the scanning depth is between 1.5 cm and 10 cm.

16. The dynamic radiation scanning system according to claim 10, wherein the radiotherapy treatment machine is a linear accelerator.

17. The dynamic radiation scanning system according to claim 10, wherein the radiotherapy treatment machine is a cobalt radiation machine.

18. The dynamic radiation scanning system according to claim 10, wherein the radiotherapy treatment machine is an electron producing machine.

* * * * *